(12) United States Patent
Mailova et al.

(10) Patent No.: US 10,201,565 B2
(45) Date of Patent: *Feb. 12, 2019

(54) GAS CONDITIONING

(71) Applicant: EndoSAT NV, Leuven (BE)

(72) Inventors: Karina Mailova, Moscow (RU); Leila Adamyan, Moscow (RU)

(73) Assignee: ENDOSAT NV, Leuven (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/714,011

(22) Filed: Sep. 25, 2017

(65) Prior Publication Data

US 2018/0071332 A1 Mar. 15, 2018

Related U.S. Application Data

(60) Continuation of application No. 14/638,243, filed on Mar. 4, 2015, now abandoned, which is a division of
(Continued)

(30) Foreign Application Priority Data

Mar. 5, 2010 (GB) .................................. 1003682.0

(51) Int. Cl.
*A61K 33/00* (2006.01)
*A61M 13/00* (2006.01)
(Continued)

(52) U.S. Cl.
CPC .............. *A61K 33/00* (2013.01); *A61K 47/02* (2013.01); *A61M 13/003* (2013.01); *A61M 13/006* (2014.02); *A61M 16/1075* (2013.01); *A61M 16/12* (2013.01); *A61M 16/16* (2013.01); *A61M 16/161* (2014.02); *A61M 2016/102* (2013.01); *A61M 2202/0208* (2013.01);
(Continued)

(58) Field of Classification Search
CPC ..... A61M 13/00; A61M 13/003; A61M 16/12
See application file for complete search history.

(56) References Cited

U.S. PATENT DOCUMENTS

| 2002/0020462 A1 | 2/2002 | Wagenheim |
| 2002/0183687 A1 | 12/2002 | Koninckx |

(Continued)

FOREIGN PATENT DOCUMENTS

| WO | 98/50064 A2 | 11/1998 |
| WO | 2004096315 A2 | 11/2004 |

OTHER PUBLICATIONS

Fabijan et al. (Abstract of: Aneasth Intensive Care 2000;28(3):270-5) 2 pages (Year: 2000).*

(Continued)

*Primary Examiner* — Ernst V Arnold
(74) *Attorney, Agent, or Firm* — Bacon & Thomas, PLLC

(57) ABSTRACT

A method for reducing or preventing mesothelial cell damage by mixing a carrier gas and between 1 volume percent and 29 volume percent of nitrous oxide gas ($N_2O$) to form a medicament and applying the medicament during surgery. The method can be used for prevention of adhesion formation, pain reduction, reducing or preventing acute inflammation, reducing or preventing $CO_2$ resorbtion or reducing tumor cell implantation upon surgery.

19 Claims, 6 Drawing Sheets

Related U.S. Application Data application No. 13/582,866, filed as application No. PCT/EP2011/053405 on Mar. 7, 2011, now abandoned.

(51) Int. Cl.

| *A61K 47/02* | (2006.01) |
|---|---|
| *A61M 16/10* | (2006.01) |
| *A61M 16/12* | (2006.01) |
| *A61M 16/16* | (2006.01) |

(52) U.S. Cl.
CPC ............... *A61M 2202/0225* (2013.01); *A61M 2202/0283* (2013.01); *A61M 2202/0468* (2013.01)

(56) References Cited

U.S. PATENT DOCUMENTS

| 2005/0107766 | A1 | 5/2005 | Ott et al. |
| 2007/0000300 | A1 | 1/2007 | Diemunsch et al. |
| 2007/0275955 | A1 | 11/2007 | Pfirrmann |
| 2008/0039911 | A1 | 2/2008 | Koninckx |
| 2009/0270794 | A1* | 10/2009 | Mantell ............... A61M 13/003 604/24 |

OTHER PUBLICATIONS

Berge, T.I. (Best Practice & Reasearch Clinical Aneasthesiology, 2001;15(3):477-483) 7 pages (Year: 2001).*

International Search Report for PCT/EP2011/053405, dated Jun. 27, 2011 (3 pages).

International Preliminary Report on Patentability and Written Opinion for PCT/EP2011/053405, dated Sep. 11, 2012 (6 pages).

Tsereteli, et al., "Prospective Randomized Clinical Trial Comparing Nitrous Oxide and Carbon Dioxide Pneumoperitoneum for Laparoscopic Surgery", pp. 173-179, (2002).

Mynbaev, et al., "Effects of Adding Small Amounts of Oxygen to a Carbon Dioxide-pneumoperitoneum of Increasing pressure in Rabbit Ventilation Models", Fertility and Sterility, vol. 92, No. 2, pp. 778-784 (Aug. 2009).

Neuman, et al., "Laparoscopy Explosion Hazards with Nitrous Oxide", Anesthesiology, vol. 78, No. 5 pp. 875-879 (May 1993).

Chinese Office Action dated Mar. 5, 2014, for CN 201180022365.9, and English translation thereof.

Cameron et al., Journal of the Royal Society of Medicine 1983, 76:1015-1018.

Ott, Chapter 1, retrieved from : http://laparoscopy.blogs.com/prevention_management/chatper_01_pneumoperitoneum;, published Jan 23, 2006.

Russian Office Action dated Mar. 3, 2015, for RU 2012142247/14, and English translation.

Jacbi et al., "The impact of conventional and laparoscopic colon resection (CO2 or helium) on intraperitoneal adhesion formation in a rat peritonitis model," Surgical Endoscopy, vol. 15, No. 4, p. 380-386.

Molinas et al., F, V&V in ObGyn 2010:2(3): 149-160.

* cited by examiner

GAS CONDITIONING

FIELD OF THE INVENTION

The present invention relates to products and systems for operation trauma prevention or reduction. More particularly, the present invention relates to compounds, e.g. for use as a pneumoperitoneum and/or gas for flowing over a body part during surgery, to systems controlling the use thereof and to methods of using such compounds or systems.

BACKGROUND OF THE INVENTION

In order to perform a laparoscopy the abdomen, which is a virtual cavity, has to be insufflated in order to create a working space. Insufflation pressure is limited to 15 mm of Hg out of fear of gas embolism, although this limit has not been substantiated clinically. $CO_2$ has been traditionally used as a gas for the pneumoperitoneum out of safety concerns. Indeed $CO_2$ has a high solubility in water and an high exchange capacity in the lungs. Therefore the risk of a gas embolism causing a hearth tamponnade should be minimal.

During laparoscopic surgery some flow through the abdominal cavity is necessary in order to evacuate smoke generated by the use of electro-surgery or of a CO2 laser. Especially the high flows used together with a CO2 laser, can induce important uncontrolled desiccation and temperature alterations in the abdominal cavity.

During open surgery, the abdominal content is directly exposed to the air with important desiccation and exposure of the superficial cells to 20% of oxygen, proven to be toxic for the mesothelial cell layer. In addition, during open surgery manipulation of bowels is more important than during laparoscopy. During open surgery the abdominal cavity is exposed to the ambient temperature.

During surgery, both laparoscopy and laparotomy, the mesothelial cells and the peritoneal cavity thus are exposed to a series of traumas such as mechanical trauma, cellular hypoxia (ie a partial pressure of oxygen less than 7 mm Hg or less than 1% of oxygen at atmospheric pressure) or hyperoxia, (i.e. a partial pressure of oxygen more than 70 mm Hg or more than 10% of oxygen at atmospheric pressure) and desiccation. The effects of these trauma's upon the mesothelial cells are additive Simultaneously surgery can be associated with important temperature changes of the cells, a decrease of temperature being rather beneficial by making cells more resistant to trauma. It is to be noticed that surgical interventions in the human occasionally may be very long interventions.

Adhesions following surgery are clinically important and cause suffering to the patients and a burden for the cost of health care. Adhesions form in the majority of men and women after surgery both after laparotomy and after laparoscopy. For example, following abdominal surgery both by laparotomy and by laparoscopy, adhesions form in over 70% of women. The clinical impact can best be illustrated as follows. Postoperative adhesions are estimated to be responsible for 30% of all chronic abdominal pain, for 30% of all infertility and for over 90% of all bowel obstructions. After abdominal surgery the incidence of reoperation and of bowel obstruction keeps rising almost linearly for at least 10 years. Re-interventions occur in some 30%, in many persons more than once, and at least 6% are linked directly to adhesion formation. Repeat surgery moreover is more difficult, more tedious and associated with more complications because of adhesions. From these findings, models have been constructed indicating an enormous cost of adhesions formation for society besides the cost of suffering of the individuals.

Adhesion formation between opposing injured peritoneal surfaces are acknowledged to be different from adhesion reformation following lysis of adhesions and from de novo adhesion formation outside the areas of surgery. Only prevention of adhesion formation has been investigated adequately. Clinical adhesion prevention in the human until today has been based upon the classic model of adhesion formation, i.e. describing adhesion as a local process between two opposing lesions.

Good surgical practice and gentle tissue handling were suggested as important by the pioneers of microsurgery. This comprised, moistening of tissues by continuous irrigation and minimal mechanical trauma.

Besides good surgical practice, adhesion prevention in the human has been limited to barriers and flotation agents with a reduction of adhesion formation that ranges for all products between 40% to 50%. It is important to note that for none of these products efficacy has been proven for endpoints that really matter, i.e. pain, infertility, bowel obstruction or reoperation rate. This can be explained by the high intra-individual variability, and the variability in surgical interventions which make adequate randomized clinical trials prohibitively large.

Sheet barriers such as Seprafilm (Hyaluronic acid-carboxymethylcellulose), Interceed (Oxidized regenerated cellulose) and Gore-tex(Expanded polytetrafluoroethylene) are proven effective but did not become very popular for various reasons. Seprafilm is difficult to use during laparoscopy whereas to be efficacious any remaining bleeding of the traumatized area should be avoided.

Since Intergel (0.5% ferric hyaluronate gel) has been withdrawn from the market, only Hyalobarrier gel(Autocross linked hyaluronic acid gel), Spraygel (Polyethylenglycol) and Intercoat/Oxiplex remain available for clinical use. Overall efficacy appears to be similar for all 3 products. A comparison between these 3 gels can unfortunately not be made since comparative trials do not exist.

Whereas in the human the efficacy of Ringers lactate as a flotation agent has not been proven, Adept, (Icodextrin) a macromolecular sugar with a higher retention time in the peritoneal cavity, was expected and shown to be efficacious in adhesion reduction. A major advantage is the safety and absence of side effects, which were well established since extensively used for peritoneal dialysis. The strength of the available evidence demonstrating efficacy, is in a Cochrane review not considered very solid.

It is beyond the scope of this application to discuss in detail the specificities of the animal models. The most comprehensive model today is the laparoscopic mouse model since most of the available products and the role of the peritoneal cavity have been investigated in detail. In this model it was demonstrated that gentle tissue handling and the conditioning of the pneumoperitoneum were the first and quantitatively the most important steps in adhesion prevention. It was demonstrated that adhesions could be decreased by humidification, by preventing mesothelial hypoxia by adding some 4% of oxygen to the $CO_2$ pneumoperitoneum, and by cooling slightly the peritoneal cavity. In this model, dexamethasone further decreased adhesions, whereas anti-inflammatory agents (NSAID's, COX1, COX2 inhibitors) and anti-TNFa monoclonals were close to ineffective.

In the mouse laparoscopic model it was equally demonstrated that adding more than 10% of oxygen to the $CO_2$ pneumoperitoneum increased adhesion formation, probably through the formation of ROS, an increase that could be diminished by decreasing the partial oxygen pressure to the normal physiologic partial pressure in peripheral cells ie between 20 and 40 mm of Hg partial oxygen (pO2) pressure.

The addition of oxygen to the pneumoperitoneum for reduction of adhesion formation has been described in WO98/50064. It has been demonstrated with $CO_2$ as carrier gas. He and $N_2O$ were suggested as alternative carrier gasses.

Prevention of angiogenesis, a consequence of hypoxia also reduces adhesion formation, as demonstrated in PIGF knockout mice and by the administration of anti VEGF and anti PIGF monoclonal antibodies.

By way of illustration, FIG. 1 indicates the effect of prevention of adhesion formation in a laparoscopic mouse model as known in 2008. Minimizing mesothelial damage by preventing desiccation, gentle tissue handling, adding oxygen and cooling decrease adhesion formation by some 75%. Adhesions can decrease further by adding Reactive Oxygen Scavengers (ROS), calcium channel blockers, phospholipids or dexamethasone. In addition Barrier gels, as used in the human, can be used achieving over 90% adhesion reduction. If in this model calcium channel blockers, phospholipids, anti-angiogenic monoclonals and fibroblast manipulation would have additional effects possibly reducing adhesion reduction by close to 100%.

SUMMARY OF THE INVENTION

It is an object of embodiments of the present invention to provide good products and systems or methods for using such products for assisting in surgery.

It is an advantage of at least some embodiments according to the present invention that these provide an efficient manner for reducing operative trauma, allowing reduction of the number of prevention means required.

It is an advantage of embodiments according to the present invention that products, systems and methods are provided allowing reduction or even prevention of adhesion formation.

It is an advantage of at least some embodiments according to the present invention that products, systems and/or methods are provided that reduce operative trauma. It is an advantage of at least some embodiments that inflammation of the peritoneal cavity can be reduced.

It is an advantage of at least some embodiments of the present invention that postoperative pain and/or morbidity can be reduced, compared with use of conventional pneumoperitoneum or open surgery.

The above objective is accomplished by a method and device according to the present invention.

The present invention relates to the use of a mixture of a carrier gas and nitrous oxide gas, the nitrous oxide gas being between 1 volume percent and 29 volume percent, for the manufacture of a medicament for reducing or preventing mesothelial cell damage.

The use may be for reducing or preventing mesothelial cell damage during surgery in a cavity by flowing the medicament in or over the cavity. The use may be for reducing or preventing mesothelial cell damage by or during pneumoperitoneum or for flow over a body during open surgery.

The mixture may comprise between 5 and 20 volume percentage nitrous oxide gas, e.g. between 5 and 10 volume percentage nitrous oxide.

The mixture furthermore may comprise between 1 and 10 volume percentage of oxygen gas.

The use may be for reducing or preventing adhesion formation.

The use may be for reducing or preventing pain.

The use may be for reducing or preventing acute inflammation.

The use may be for reducing or preventing $CO_2$ resorbtion.

The use may be for tumor implantation reduction.

The carrier gas may be carbon dioxide gas.

The solubility of the carrier gas may be larger than 0.5 g/l in water.

The present invention also relates to the use of a compound comprising a mixture of a carrier gas and between 1 volume percent and 29 volume percent nitrous oxide gas ($N_2O$) for the manufacture of a medicament for reducing or preventing adhesion formation.

The use may be for the manufacturing of a medicament for reducing or preventing adhesion formation by or during pneumoperitoneum or for flooding of flowing over a body cavity or surface during open surgery.

The compound may comprise between 5 and 20 volume percentage nitrous oxide gas, more preferably between 5 and 10 volume percentage nitrous oxide gas.

The compound may furthermore comprise between 1 and 10 volume percentage oxygen gas.

The present invention also relates to conditioning system for use in surgery, the gas supply system comprising a gas supplying means adapted for providing a mixture of gas in or over a cavity wherein surgery is performed, the gas supply system being adapted for providing a mixture of gas using for use in surgery, characterized in that the gas supply system is designed to supply gas mixtures comprising a carrier gas and between 1 volume percent and 29 volume percent nitrous oxide gas ($N_2O$).

The gas supplying means may be an endoscopic insufflation means for supplying the gas mixture as pneumoperitoneum.

The gas supplying means may comprise a gas location means comprising upstanding walls for maintaining the gas mixture at the cavity wherein surgery is performed.

The gas supply system may be designed to supply gas mixtures comprising between 5 and 20 volume percentage nitrous oxide gas.

The carrier gas may be carbon dioxide.

The gas supplying means may be designed to provide between 1 and 10 volume percentage oxygen gas.

The gas supplying means may comprise a mixing unit for mixing individual gasses from individual gas supplies.

The gas supplying means may comprise a moistening means for moistening the gas mixture.

The conditioning means may comprise a sprinkler for directly moistening the cavity. The sprinkler may be separate from the moistening means for moistening the gas mixture. The conditioning system may be adapted for distributing a medicine, drug or chemical through the sprinkler.

The gas supplying means may comprise a heating and/or cooling means for controlling the temperature of the gas mixture.

The gas supplying means may comprise a controller for system comprises a controller being programmed for supplying the gas mixture.

The controller may be programmed for initially providing a gas or gas mixture comprising the carrier gas but no nitrous oxide gas and for increasing the nitrous oxide gas concentration thereafter to supply the gas mixture.

The controller furthermore may be programmed for controlling the ratio nitrous oxide gas to carrier gas in the mixture.

The controller furthermore may be programmed for controlling the ratio nitrous oxide gas to carrier gas in the mixture according to a predetermined dynamic ratio.

The gas supplying means may comprise an aspiration means for removing gases from a living creature and/or from a surgical area.

The controller furthermore may be programmed for providing between 1 and 10 volume percentage oxygen gas.

The controller furthermore may be adapted for controlling the temperature of the gas mixture and/or humidity of the cavity.

The conditioning means furthermore may comprise any of a ROS scavenger providing means, a calcium channel blockers and phospholipids providing means, a dexamethasone providing means, a barrier gel providing means or a means for providing anti-angeiongic factors or fibroblast manipulation means. The present invention relates to a compound for use in surgery, the compound comprising a mixture of a carrier gas and between 1 volume percent and 29 volume percent nitrous oxide gas ($N_2O$). It is an advantage of embodiments according to the present invention that addition of nitrous oxide gas results in the reduction of operative trauma. It is an advantage of at least some embodiments of the present invention that reduction of adhesion formation can be obtained. The compound may comprise between 5 and 29 volume percentage nitrous oxide gas, e.g. between 5 and 20 volume percentage nitrous oxide gas, e.g. between 5 and 10 volume percentage nitrous oxide gas. It is an advantage of embodiments according to the present invention that only a limited amount of nitrous oxide gas is required, as nitrous oxide gas carries a potential explosion risk when used in concentrations higher than 29%. Considering the risk of gas embolism nitrous oxide moreover is safe considering its high solubility comparable to $CO_2$ in water (solubility of 1.5 and 1.45 g/l for N2O and CO2 respectively). It has been found that $N_2O$ concentration advantageously is at least 5 volume percentage as for concentrations lower than 5 volume percentage effects of adhesion prevention are less pronounced, e.g. using 3 volume percentage of $N_2O$ in the pneumoperitoneum resulted in about 70% effectiveness and using 1 volume percentage of $N_2O$ resulted in about 50% effectiveness. It is an advantage of embodiments according to the present invention that the use of a gas mixture comprising between 1% to 29% $N_2O$ results in adhesion prevention, pain reduction and other advantageous effects in the first days after surgery.

The compound furthermore may comprise between 1 and 10 volume percentage oxygen. It is an advantage of embodiments according to the present invention that also oxygen gas can be added to the gas mixture, as oxygen gas provides an additive effect in prevention or reduction of adhesion formation. Oxygen however has a very low solubility of 0.0391 g/l in water.

The compound may be a pneumoperitoneum.

The compound may be a gas reducing or preventing adhesion formation.

The carrier gas may be carbon dioxide gas.

The compound may have a carrier gas having a solubility larger than 0.5 g/l in water.

The compound may be a medicament or a basis therefore.

The present invention also relates to a controller for controlling a gas supply system, the controller being programmed for supplying a mixture of a carrier gas and between 1 volume percent and 29 volume percent nitrous oxide gas ($N_2O$). The controller may be programmed for supplying the mixture with between 5 and 20 volume percentage nitrous oxide gas, more preferably between 5 and 10 volume percentage nitrous oxide gas. The controller may be programmed for initially providing a gas or gas mixture comprising the carrier gas but no nitrous oxide gas and for increasing the nitrous oxide gas concentration thereafter to supply the gas mixture. It is an advantage of embodiments according to the present invention that first a good soluble gas may be used for insufflation in order to prevent gas embolism, where after nitrous oxide gas can be introduced, either after a predetermined time or upon activation of the user of the system. The controller furthermore may be programmed for controlling the ratio nitrous oxide gas to carrier gas in the mixture. The controller furthermore may be programmed for controlling the ratio nitrous oxide gas to carrier gas in the mixture according to a predetermined dynamic ratio. The controller furthermore may be programmed for providing between 1 and 10 volume percentage oxygen gas. The controller furthermore may be adapted for controlling the temperature of the gas mixture. It is an advantage of embodiments of the present invention that temperature control can easily be taken into account, as temperature is a further factor that may assist in the prevention or reduction of adhesion formation. The controller furthermore may be adapted for in addition humidification of the gas mixture. It is an advantage of embodiments of the present invention that humidification control can easily be taken into account, as also humidification is a further factor that may assist in the prevention or reduction of adhesion formation.

The present invention also relates to a gas supply system for supplying gas, the gas supply system comprising a gas supplying means for providing a mixture of gas for use in surgery, characterized in that the gas supply system is designed to supply gas mixtures comprising a carrier gas and between 1 volume percent and 29 volume percent nitrous oxide gas ($N_2O$). The gas supply system may be designed to supply gas mixtures comprising between 5 and 20 volume percentage nitrous oxide gas, more preferably between 5 and 10 volume percentage nitrous oxide gas. The carrier gas may be carbon dioxide. The gas supply system may be designed to provide between 1 and 10 volume percentage oxygen gas. The gas supply system may comprise a mixing unit for mixing individual gasses from individual gas supplies. The gas supply system may comprise a moistening means for moistening the gas mixture. The gas supply system may comprise a heating and/or cooling means for controlling the temperature of the gas mixture. The gas supply system may comprise a controller as described above. The gas supply system may comprise an endoscopic insufflation means for supplying the gas mixture as pneumoperitoneum. The gas supply system may comprise an aspiration device for removing gases from the body and optionally also from the operation area.

A method for reducing or preventing mesothelial cell damage, e.g. for reducing or preventing adhesion formation or e.g. reducing or preventing mesothelial cell damage by or during pneumoperitoneum or for flow over a body during open surgery, or e.g. reducing or preventing pain, or reducing or preventing acute inflammation, e.g. or reducing or preventing $CO_2$ resorbtion, by using a compound comprising a mixture of carrier gas and between 1 volume percent and 29 volume percent nitrous oxide gas ($N_2O$). The method may be using the gas mixture by or during pneumoperitoneum or during open surgery. The method may be using the gas mixture as insufflating gas, in which the gas mixture comprises between 5 and 20 volume percentage nitrous oxide gas, more preferably between 5 and 10 volume percentage nitrous oxide gas. The method may be by using a gas mixture furthermore comprising between 1 and 10 volume percentage oxygen gas.

The method may comprise administering the compound to a living creature in need of an adhesion reduction or preventing treatment. The method furthermore may comprise at least one of providing cooling, providing ROS scavengers, providing calcium channel blockers and phospholipids, providing dexamethasone, providing barrier gels and providing anti-angiongenic factors or fibroblast manipulation.

The present invention also relates to a method for reducing or preventing adhesion formation in open surgery by using a compound comprising a mixture of carrier gas and between 1 volume percent and 29 volume percent nitrous oxide gas ($N_2O$) and/or between 1 volume percent and 10 volume percent oxygen gas.

The present invention also relates to a method for reducing tumor implantation by using a compound comprising a mixture of carrier gas and between 1 volume percent and 29 volume percent nitrous oxide gas ($N_2O$).

The present invention also relates to a method for applying anesthesia to a living creature, the method comprising providing anesthetic compound for blocking sensation in a living creature, wherein providing anesthetic compound comprises adjusting a doses of the anesthetic compound taking into account the provision of a mixture comprising between 1 volume percent and 29 volume percent of nitrous oxide gas by or during pneumoperitoneum or during open surgery for adhesion prevention.

It is an advantage of embodiments according to the present invention that $N_2O$ at low concentrations is virtually without side effects and that it is a gas known and used in medicine.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
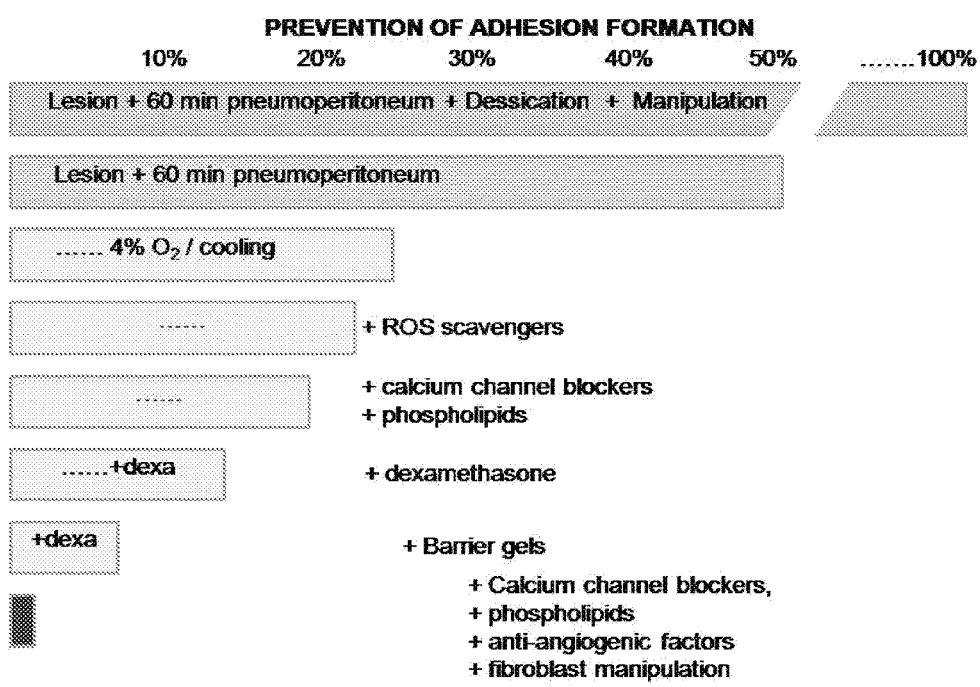
FIG. 1 illustrates an overview of methods and techniques for prevention of adhesion formation as used in prior art, the overview indicating the obtained adhesion formation prevention in a laparoscopic mouse model.

The drawings are only schematic and are non-limiting. In the drawings, the size of some of the elements may be exaggerated and not drawn on scale for illustrative purposes.

DETAILED DESCRIPTION OF THE INVENTION

Where in embodiments of the present invention reference is made to nitrous oxide gas, also known as happy gas or laughing gas, reference is made to the chemical compound having the chemical formula $N_2O$. At room temperature, it is a colorless http://en.wikipedia.org/wiki/Gas.

Where in embodiments of the present invention reference is made to gas that is introduced in a cavity of the body of a living creature lined by a mesothelium reference is made to the abdominal cavity, the pericardium and the lung pleura of an animal or human being. More particularly, in embodiments of the present invention, reference is made to gas that is deliberately created, e.g. by the surgical team, for insufflating a cavity of the body of a living creature, e.g. the abdomen, and to gas that is deliberately introduced in during laparotomy or laparoscopy or over the body of a living creature during open surgery for removing environmental air or unwanted gas present.

Where in embodiments of the present invention reference is made to laparotomy, reference is made to a surgical procedure involving an incision through the wall of the cavity, e.g. the abdominal wall, to gain access into the abdominal cavity. Where in embodiments of the present invention reference is made to laparoscopy, reference is made to an operation performed with the aid of an endoscope and a camera e.g. in the abdomen or pelvis through small incisions.

Where in embodiments of the present invention reference is made to open surgery, reference is made to surgery whereby large incisions are made, so that surgery can be performed without the aid of a camera and/or endoscope.

Where in embodiments of the present invention reference is made to a compound, the latter includes the combination of the products described with gels, e.g. for use in endoscopy.

Embodiments of the present invention relate to products, also referred to as compounds, e.g. pneumoperitoneum products, and systems and methods using such products, e.g. pneumoperitoneum products, for assisting in surgery. It is an advantage of embodiments according to the present invention that a reduction of adhesion can be obtained, compared to the currently used techniques. Although the exact process of adhesion formation still seems unclear, by way of illustration, some principles on which adhesion formation could be based are provided. Mesothelial cells form a monolayer resting on a basal membrane and an underlying connective tissue lining the organs and the wall of the abdominal cavity, of the pleura and of the pericardium. While the exact origin of mesothelial cells remains debated they remain crucially important for peritoneal repair and of adhesion formation. The roles of mesothelial cells in maintaining normal serosal membrane integrity and function is still only partially understood. They secrete glycosaminoglycans and surfactant to allow the parietal and visceral serosa to slide over each other. They actively transport fluids, cells and particulates across the serosal membrane and actively modulate gas resorbtion as $CO_2$ e.g. from the pneumoperitoneum. They synthesize and secrete mediators which play important roles in the inflammatory, immune and tissue repair responses. The peritoneal cavity contains fluid which should be considered a specific micro-environment with protein and hormone concentrations which are much different from plasma.

When the mesothelial cell becomes traumatized for example by hypoxia during $CO_2$ pneumoperitoneum, the large flat mesothelial cell retracts, known as 'bulging of cells', and the highly specialized layer of contiguous peritoneal cells is transformed into a layer of individual cells and between these cells large areas of basal membrane is directly exposed. Similar effects are believed to occur in response to all types of trauma such as dessication, mechanical or chemical trauma. The consequence of this effect will affect at least transport of substances which transport is actively regulated by the mesothelium layer such as the resorbtion of $CO_2$ from the pneumoperitoneum. Diffusion of larger molecules probably is greatly enhanced.

Figure 2:
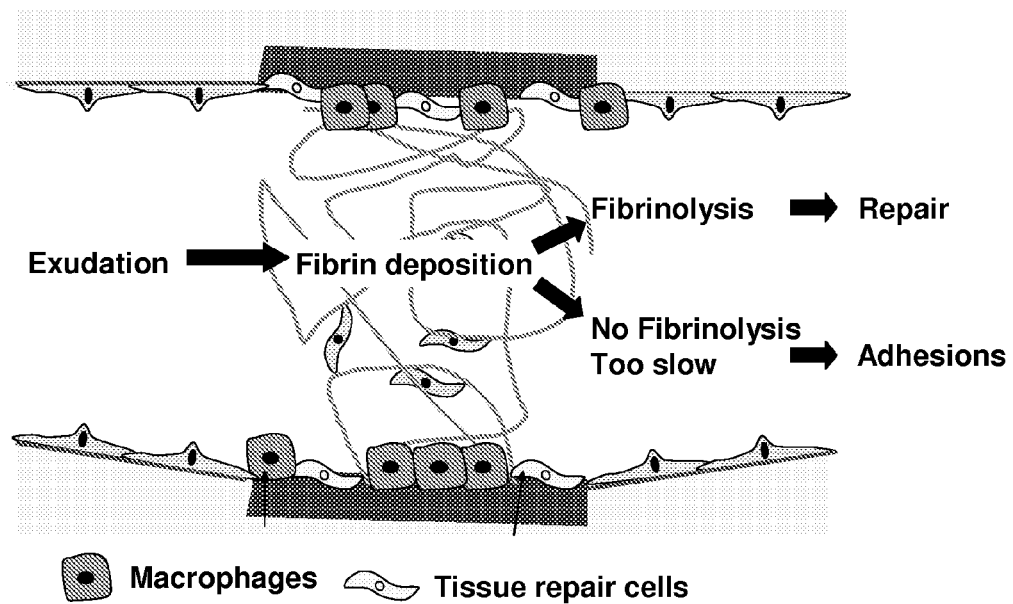
FIG. 2 illustrates a first model for explaining adhesion formation, illustrating principles assumed for adhesion formation which can be reduced using embodiments of the present invention.

According to a classic model of adhesion formation, as shown in FIG. 2, a trauma of the peritoneum is followed by a local inflammatory reaction, exudation and fibrin deposition. This fibrin is normally rapidly removed by fibrinolysis while simultaneously the peritoneal repair process is started. Within hours after injury, the injured area is covered by what is believed macrophages and 'tissue repair cells, which within 3 to 4 days differentiate into mesenchymal cells. Repair starts specifically from numerous small islands and the repair of small and large areas therefore is similar. If the normal rapid repair of peritoneal lesions fails or when repair is delayed other processes which also were activated become dominant. Within 4 to 6 days fibroblast proliferation invading the fibrin scaffold and angiogenesis start, leading invariably to adhesion formation. The importance of the fibrin scaffold between 2 injured surfaces was elegantly demonstrated since separating these areas by silastic membranes for up to 30 hours abolished adhesion formation. This type of experiments, reinforced the belief that adhesion formation is a local process and that prevention should aim at separating the surfaces for at least to 2 days. Medical treatment given intravenously or intraperitoneally is considered less important since this type of treatment would have difficulties to reach the injured zone because of local ischemia and since it is shielded by the fibrin plug. The pathophysiology of this local process has been considered an inflammatory reaction, with players and mechanisms as fibrinolysis, plasmin activation and PAI's, local macrophages and their secretion products and the overall oxygenation of the area or the absence thereof, driving angiogenesis, fibroblast proliferation and mesothelial repair.

Little is known about the mechanisms which determine whether adhesions will be velamentous, thick and or vascularised and which factors determine innervations. Also adhesion remodeling is something which is poorly understood.

Figure 3:
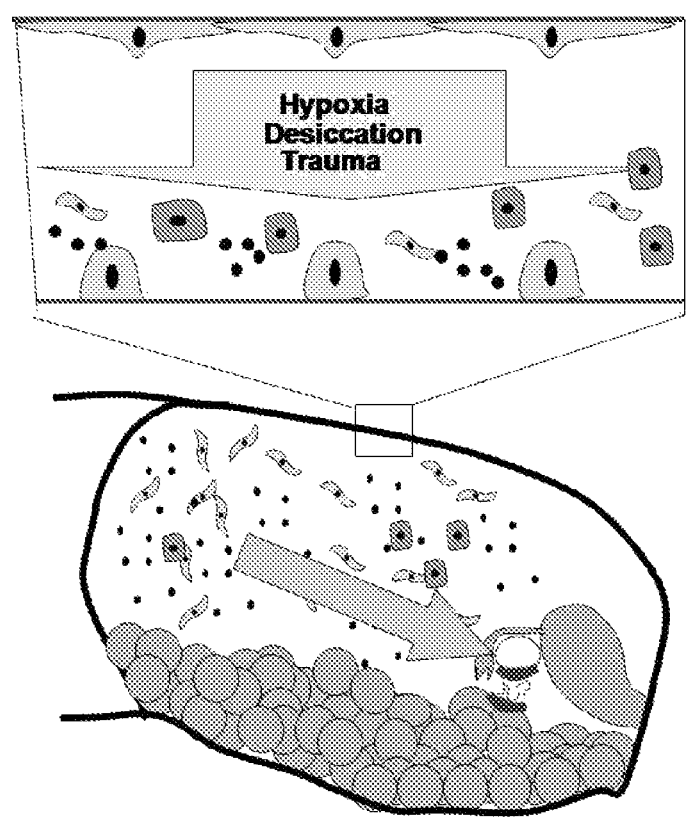
FIG. 3 illustrates an updated model compared to FIG. 2 for explaining adhesion formation, illustrating principles assumed for adhesion formation which can be reduced using embodiments of the present invention.

During the last decade evidence has accumulated that the entire peritoneal cavity is a cofactor in adhesion formation, which has resulted in an updated model, as indicated in FIG. 3. Identified so far in laparoscopic rabbit and mouse models for adhesion formation are dessication, hypoxia, reactive oxygen species (ROS) and manipulation which cause inflammation of the entire peritoneal cavity and increase adhesion formation at the injured area.

$CO_2$ pneumoperitoneum may induce mesothelial hypoxia, retraction of mesothelial cells exposing directly the extracellular matrix, the attraction into peritoneal fluid of substances or cellular elements, that enhance adhesion formation and/or decrease repair. Although one might argue that these factors as hypoxia, hyperoxia and dessication, also affect the injured site the observation that manipulation in the upper abdomen only, also increases adhesions with inflammation of the entire cavity demonstrates that the entire peritoneal cavity can be a cofactor in adhesion formation.

The trauma caused mechanically by manipulation or through hypoxia, hyperoxia and ROS, and dessication, all cause an inflammatory reaction not only at the level of the lesions but of the entire peritoneal cavity. This inflammatory reaction must increase mediators in peritoneal fluid enhancing adhesion formation. The pathophysiology of some factors have been well demonstrated, as the mesothelial hypoxia by pure $CO_2$ pneumoperitoneum. Indeed, whereas the mesothelial layer stains hypoxic, the increase in adhesions is prevented by the addition of 3-4% of oxygen (restoring the physiologic intraperitoneal partial oxygen pressure of 30 to 40 mm Hg), and the effect is absent in mice partially deficient for HIF1a (hypoxia inducible factor) and in HIF2a the hypoxemia response factors being the first to be activated by hypoxia.

The classic model that views adhesion formation as a local phenomenon, enhanced or modulated by factors from the entire peritoneal cavity may be considered as complementary. The peritoneal cavity may be an important cofactor in adhesion formation. It has been found that compared to the adhesions that form after an opposing surgical lesion only, $CO_2$ pneumoperitoneum may increase adhesions five fold through mesothelial hypoxia, and if used together with bowel manipulation adhesions increase up to 20 times. Recent experiments on acute inflammation moreover have confirmed that a surgical lesion is necessary to initiate adhesions, but that factors from the peritoneal cavity are quantitatively the most important.

Both models also are important for the understanding of adhesions prevention agents. A flotation agent will also dilute peritoneal fluid and any factor secreted locally by the denuded areas, and will hamper the access. Barriers on the other hand might in addition to keep tissues separated, shield the injured area from the peritoneal fluid and its constituents.

Clinically some individuals form more easily adhesions after surgery than others, an observation supported by the fact that some mice strains form much more adhesions than others, while variability of adhesion formation is much lower in inbred strains.

The present invention will now be described with reference to a number of aspects and embodiments, the present invention not being limited thereto.

In a first aspect, the present invention relates to a product, also referred to as compound, and to the use of such a compound for the manufacture of a medicament. The use may be for reducing or preventing mesothelial cell damage during surgery in a cavity by flowing the medicament in or over the cavity. Different types of surgery thereby are envisaged. When endoscopy is applied, which also may be referred to as minimal access surgery and which typically may be advantageous because of a decreased postoperative morbidity, less pain and a shorter hospitalization, the cavity wherein surgery or inspection is required typically requires insufflation to create a distention for creating visibility in the cavity. Typically carbon dioxide gas is used for this, especially in the case of intra-abdominal endoscopy, for safety reasons. Carbon dioxide gas however, irritates the peritoneum and enhances adhesion formation. Similarly in open surgery the 20% oxygen concentrations (e.g. higher than 10%) in environmental air also result in cellular damage and operative trauma. The compound according to the present invention may be used as pneumoperitoneum as well as gas for flowing over the body during open surgery. Applying a compound according to embodiments of the present invention as or in pneumoperitoneum or as a gas flow flowing over the cavity for removing environmental air or other unwanted gasses allows reducing or preventing operative trauma as it assists in reduction or prevention of adhesion formation. The compound comprises a carrier gas, such as for example carbon dioxide gas ($CO_2$), and between 1% and 29% nitrous oxide gas ($N_2O$). The upper limit thereby is amongst others determined by some explosion risk at higher concentration. In some embodiments, the compound consists of a carrier gas and nitrous oxide gas ($N_2O$), and no other components are intentionally added to the compound. The carrier gas advantageously is a soluble carrier gas. It may for example have a solubility in water larger than 0.5 g/l. It has surprisingly been found that the use of nitrous oxide gas has advantageous effects on reduction or prevention of adhesion formation. The compound may in some embodiments for example comprise between 1 and 29 volume percentage nitrous oxide gas, preferably between 5 and 20 volume percentage nitrous oxide gas, more preferably between 5 and 10 volume percentage nitrous oxide gas. The remaining part may be or may mainly be the carrier gas, such as for example pure carbon dioxide gas. Obviously other gases, such as helium, could be used as carrier gas, although this would conflict with the safety requirements during laparoscopy. $CO_2$ is generally used for pneumoperitoneum since $CO_2$ is highly soluble in water and since $CO_2$ has a high exchange capacity in the lungs. The addition of a small amount of gas, e.g. less than 10% of a non soluble gas to the compound is considered clinically safe for gas embolism.

The compounds described according to the present invention have not been used for reduction or prevention of adhesion formation, in particularly not by or during pneumoperitoneum. The compounds, which also may be referred to as drugs, can be applied either systemically or by local instillation during surgery or by the prolonged administration intraperitoneally postoperatively, preferably locally, e.g. by miniosmotic pumps. Local administration has the advantage that much higher concentrations of active drugs or compounds can be provided by providing them over longer time. The administration can be performed for a plurality of hours postoperatively.

In one embodiment, the compound also may be moistened. As drying of peritoneal surfaces has been considered another cofactor in adhesion formation, moistening the compound used for preventing adhesion formation results in an additional reduction of adhesion formation.

In one embodiment, the compound also may comprise oxygen gas in the gas mixture. It has surprisingly been found that the effect of oxygen and the effect of nitrous oxide gas have additive effects, so that combining both oxygen gas and nitrous oxide gas in the gas mixtures results in advantageous reduction or prevention of adhesion formation. The compound thus may comprise carbon dioxide as major component, with additional nitrous oxide gas and oxygen gas. The concentration of oxygen gas used may be in the range 1% to 10%, e.g. 2% to 6%, e.g. 3%.

In one embodiment, together with the use of the gas mixture comprising nitrous oxide gas, one or more of the following mechanisms and/or drugs can be used for the prevention of adhesion formation. It thereby is an advantage that the use of nitrous oxide comprising gas mixtures allows easy combination and provides additional advantages. The drugs or mechanisms used may be one or more of drugs administered continuously or intermittently via aerosol, activation of potassium channels, modulation of macrophage activation and leucocyte attraction through cytokines, or their inhibitors, the effect of VEGF expression being blocked by antibodies or other inhibitors, indomethacin which can inhibit the membrane lipid peroxidation products following anoxemia, prostaglandin E1 for reducing the consequences of ischemia and/or anoxemia in the liver, allopurinol for reducing the consequences of ischemia and/or anoxemia in the kuppfer cells of the liver through an effect on xanthine-oxidase, calcium channel blockers, free radical scavengers, lipid peroxysomes, pregnatrienes, calcium antagonists, prevention of hypoxia associated stress proteins, acidosis for preventing reperfusion damage, MP, dopamine and ATP-MgCl2 administered following the anoxemia. The dose of the above drugs or systems is determined taking into consideration the age, sex, and symptom of the disease of the subject, the desired therapeutic effect, the period of administration, etc. Further features and advantage of the compound will become apparent in the examples. As indicated above, in some embodiment, the products and methods as described above are applied for open surgery and the gas mixture may be supplied through a tube that is positioned in or near the cavity in the living creature, opened for surgery. The present invention according to embodiments of the present invention also relates to a method of preventing or reducing adhesion formation by providing a gas mixture to the cavity opened for performing open surgery. The gas mixture thereby may in one embodiment comprise a carrier gas and between 1 and 10 volume percent of oxygen, e.g. between 2 volume % to 6 volume %, e.g. 3 volume %. Alternatively or in addition thereto, the gas mixture may be nitrous oxide, more particularly between 1 and maximally 29 volume % and if used together e.g. with 4% of oxygen to maximally 25 volume %, e.g. between 5% and 20% or between 5% and 10%.

Figure 4:
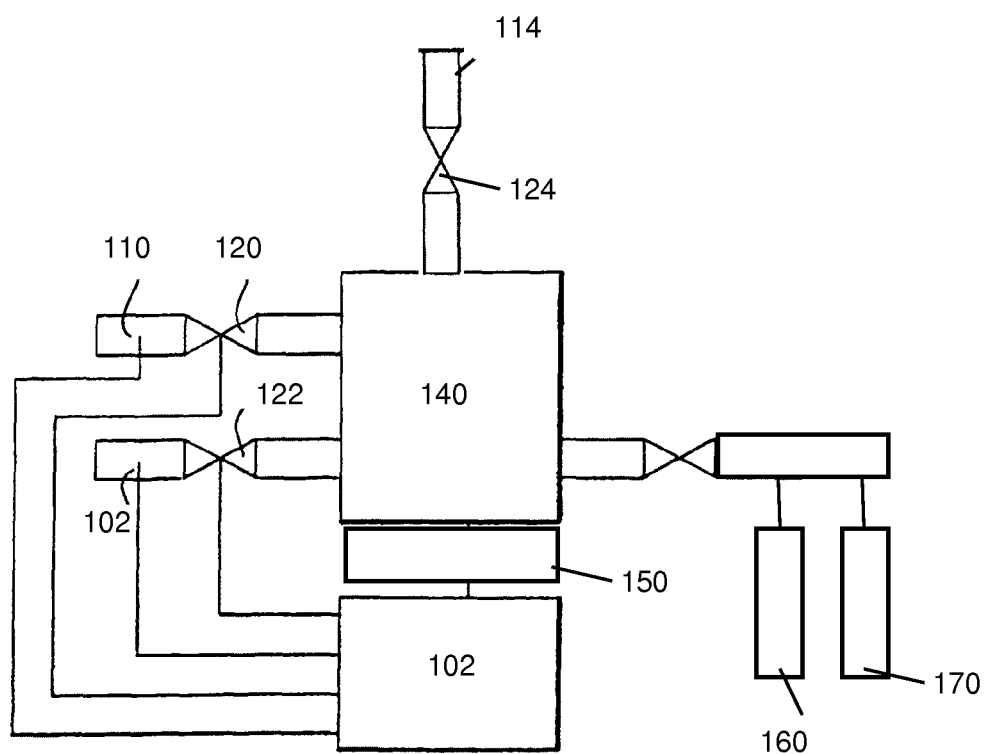
FIG. 4 illustrates an example of a system for using $N_2O$ gas as component in a compound, according to an embodiment of the present invention.

In one aspect, the present invention also relates to a gas supply system or conditioning system comprising a gas supplying system or gas supplying means for supplying a gas flow during surgery. The system in some embodiments advantageously may be an endoscopic system, although embodiments of the present invention are not limited thereto. In applications for open surgery for example, typically non-endoscopic systems may be used. A gas supply system or conditioning system comprising a gas supplying system or gas supplying means according to embodiments of the present invention comprises a gas supplying means for providing a mixture of gas for use in surgery. The gas supply system furthermore is designed for supplying gas mixtures comprising a carrier gas, such as e.g. carbon dioxide gas, and nitrous oxide gas for reduction or prevention of adhesion formation. According to embodiments of the present invention, the nitrous oxide gas thereby is present in a concentration from the range 1% to 29%, e.g. from the range 5% to 20%, e.g. from the range 5% to 10%. Depending on the application, the gas supply system may comprise an endoscopic insufflation means or a gas supply means for use in open surgery. It was surprisingly found that nitrous oxide gas reduces adhesion formation during or by pneumoperitoneum as well as when used for flowing over bodily parts for removing environmental air or other unwanted gasses. The gas supply system may be designed or programmed for supplying a gas mixture comprising between 1 and 29 volume percentage nitrous oxide gas, e.g. between 5 and 20 volume percentage nitrous oxide gas, e.g. between 5 and 10 volume percentage nitrous oxide gas. The gas supply system furthermore may be designed for additionally supplying in the gas mixtures between 1 and 10 volume percentage of oxygen gas, e.g. between 2 and 6 volume percentage of oxygen gas, or e.g. 3 volume percentage oxygen gas. The gas supply system may have a number of gas inlets through which the different gasses are received or one of more gasses may be in a premixed form. The gas supply system may comprise a mixing system for mixing individual received gasses from individual gas supplies. In one embodiment, the system furthermore may comprise a moistening means for moistening the gas mixture that will be supplied. Alternatively or in addition thereto a moistening means also may be present for directly moistening the bodily parts in the cavity. The moistening system may in one embodiment be a sprinkler system. The gas supply system also may comprise a heating and/or cooling means for heating and/or cooling of the gas mixture. The latter may be performed in response to a temperature measurement, i.e. the gas supply system also may comprise a temperature measurement system for obtaining temperature information for the gas mixture. An appropriate temperature may be one of the cofactors influencing the adhesion formation. The gas supply system also may comprise a controller for controlling the gas mixture and properties thereof. The controller may be programmed such that a predetermined ratio, or if it is desired to vary this over time, a predetermined ratio profile for the nitrous oxide gas can be obtained. The controller may provide control signals to controllable valves at the gas inlets, in order to control the amount of gas of a certain type that is provided for making the gas mixture. Such valves, which typically also are part of the gas supply system, may be mechanical valves, electromechanical valves, etc. The controller in such way may be adapted for setting the desired ration of nitrous oxide gas to carbon oxide gas as well as to alter it. In one embodiment, such a controller may be programmed to initially provide a gas mixture with soluble gas such as for example carbon dioxide while after a predetermined time or upon a predetermined command, the gas mixture may be altered to comprise a fraction of nitrous oxide gas. The controller may, in some embodiments, also be adapted for switching between a first gas or gas mixture and a second gas mixture, e.g. from a gas or gas mixtures not comprising nitrous oxide gas to a gas mixture comprising nitrous oxide gas in a predetermined ratio. The controller furthermore may be adapted for controlling the moistening system, the heating and cooling device, etc. In an advantageous embodiment, the gas supply system may be adapted with a sensing unit wherein one or more environmental parameters such as temperature, humidity, gas composition, etc. can be measured near the bodily parts or in the cavity, so that feedback can be provided in order to optimize the parameter settings. By way of illustration, embodiments of the present invention not being limited thereto, an example of a gas supply system is shown in FIG. 4. In FIG. 4 a gas supply system 100 comprising a controller 102 programmed for controlling the provision of a gas mixture comprising carbon dioxide and nitrous oxide gas in a given ratio or with a predetermined ratio profile is shown. In the example, at least two gas inlets 110, 112 are provided, one for carbon dioxide and one for nitrous oxide gas e.g. equipped with electromechanical valves 120, 122. In one embodiment, a third gas inlet 114 equipped with a valve 124, e.g. an electromechanical valve, may be provided for also controlling the inlet of oxygen as. Mixture is obtained by periodically opening valves 120, 122 thus mixing the two gasses in a mixer, e.g. buffer volume. The system furthermore may comprise pressure sensors for controlling the flow of gases and may for example be programmed for obtaining a predefined pressure difference between the buffer volume 140 and the incoming gas flows.

Alternatively or in addition thereto, also a feedback system 150 may be provided adapted for compensating, e.g. in an automated and/or automatically manner, deviation from a predefined composition by controlling proportional valves at the gas inlet. Such a system has the advantage of providing a quasi immediate response to a change in the mixing ratio or to a request for such a change. The controller 102 also may be programmed for providing a gas mixture having a predetermined dynamic composition over time. A moistening means 160, e.g. sprinklers, and a heating and/or cooling means 170, e.g. a heating element or cooling element, for controlling the temperature of the gas mixture also may be provided.

In one embodiment, the gas supply system also may be provided with a system for aspiration, i.e. removal of gases from the body with a suction device. Such a system may prevent anesthetic nitrous oxide from flowing in the air near the operating field, optionally forming a risk for medical personnel. During the surgery, aspiration thus may be performed using a suction device. The gas could be reused in closed circuit after filtrating of particulates but this is not done until today since the gas would have to be recompressed for in an insufflator for endoscopic surgery. In open surgery however, we can take advantage of the density of $CO_2$ and $N_2O$ by constructing an aspiration system, for applying aspiration e.g. a circular aspiration system on and around the operation wound. This not only would prevent the $N_2O$ flowing into the operating theatre but would in addition protect the surgeon from inhalation of particulates generated by vaporization.

In one aspect, the present invention also relates to a controller for controlling the gas mixture used. Such a controller may be as the controller described above. The controller may be implemented in hardware as well as in software. It may be a processing system that may comprise instructions for performing controlling functions of a controller as described above or as described in any of the method embodiments.

It is an advantage of embodiments according to the present invention that using $N_2O$ adhesion formation can be reduced or even prevented. This surprising effect can for example be seen for a concentration of 5% of $N_2O$ and an additional effect can be seen when adding e.g. 3% of oxygen.

It is an advantage of embodiments according to the present invention that e.g. the use of 5% $N_2O$, alone or in combination with 3% of $O_2$ in the pneumoperitoneum will reduce postoperative pain and postoperative inflammation.

It is an advantage of some embodiments of the present invention that reduced adhesion formation and/or reduced postoperative pain or postoperative inflammation also can be obtained for open surgery by insufflating in the lower parts of the abdomen gas comprising $N_2O$ in order to prevent air to reach the mesothelial cells. Decrease of adhesion formation, postoperative pain and postoperative abdominal inflammation are best obtained by using such a gas flow, in combination with humidification and constant slightly lower temperature. The gas mixture may comprise $N_2O$ and oxygen, e.g. in one example being 5% $N_2O$ and 3% of Oxygen.

In some embodiments, the use of additional $N_2O$ in the gas mixture used for flowing in/or over the cavity in which surgery is taking place is combined with cooling of the cavity, e.g. using sprinklers, adding oxygen to the gas mixture, using dexamethasone, or other features indicated in FIG. 1 and allowing conditioning of the cavity.

By way of illustration, embodiments of the present invention not being limited thereto, some examples are discussed below, illustrating some features and advantages of some embodiments according to the present invention.

In a first example, during laparoscopic experiments on adhesion formation in rabbits $CO_2$ with 25% of $N_2O$ was used in order to reduce the need of anaesthesia during these experiments. Surprisingly, it was not possible to induce adhesions in these rabbits.

In a second set of examples, adhesion formation in mice is studied. The investigations were performed in a 12-13-week-old female Balb/c mice weighting 20 to 30 g. Before surgery, the animals were kept under standard laboratory conditions (temperature 20° C.–22° C., relative humidity 50%-60%, 14 hours light and 10 hours dark). They were fed with a standard laboratory diet (MuraconG, Carsil Quality, Turnhout, Belgium) with free access to food and water at any time.

The experiments were performed under following conditions. The model used consisted of $CO_2$ pneumoperitoneum-enhanced adhesions following a mechanical bipolar lesion during laparoscopy. The pneumoperitoneum was maintained for 60 minutes using, in the reference measurement, pure and humidified $CO_2$ at 15 mmHg of insufflation pressure. In order to control temperature, animals and equipment, i.e. insufflator, humidifier, water valve, ventilator and tubing, were placed in a closed chamber maintained at 37° C. (heated air, WarmTouch, Patient Warming System, model 5700, Mallinckrodt Medical, Hazelwood, Mo.). The insufflation gas temperature was determined by the environmental temperature, i.e. at 37° C. Because anaesthesia and ventilation can influence body temperature and body temperature can influence adhesion formation, the timing and temperature were strictly controlled. The time of the anaesthesia injection was considered time 0 (T0). The animal preparation and ventilation started after exactly 10 minutes (T10). The pneumoperitoneum started at 20 minutes (T20) and was maintained for 60 minutes until T80.

Animals were anesthetized at T0 with i.p. pentobarbital (Nembutal, Sanofi Sante Animale, Brussels, Belgium) with a dose of 0.08 mg/g. Animal preparation, i.e. shaving, positioning to the table in the supine position, intubation and ventilation started after 10 min exactly (T10). Animals were intubated with a 20-gauge catheter and ventilated with a mechanical ventilator (Mouse Ventilator MiniVent, Type 845, Hugo Sachs Elektronik-Harvard Apparatus GmbH, March-Hugstetten, Germany) using humidified air with a tidal volume of 250 µl at 160 strokes/min. The experiments started at T20 (i.e. 20 minutes after initial anesthesia) and ventilation finished at T80 (i.e. 80 minutes after initial anesthesia). This strict timing from anaesthesia onwards is important not to introduce temperature differences and thus variability in adhesion formation in the mice due to anaesthesia and manipulation.

The surgical procedures were standard opposing bipolar lesions. At T20, the $CO_2$ pneumoperitoneum was induced using a Thermoflator (as available from Karl Storz, Tüttlingen, Germany) through a 2 mm endoscope with a 3.3 external sheath for insufflation (as available from Karl Storz, Tüttlingen Germany) introduced into the abdominal cavity through a midline incision caudal to the xyphoid appendix. The incision was closed gas tight around the endoscope in order to avoid leakage. The insufflation pressure was 15 mmHg. For humidification, the Storz Humidifier 204320 33 (as available from Karl Storz, Tüttlingen, Germany) was used. After the establishment of the pneumoperitoneum, two 14-gauge catheters (Insyte-W, Vialon, Becton Dickinson, Madrid, Spain) were inserted under laparoscopic vision in order to create some flow through the abdominal cavity. Standardized 10 mm×1.6 mm lesions were performed in the antimesenteric border of both right and left uterine horns and in both the right and left pelvic side walls with bipolar coagulation (20 W, standard coagulation mode, Autocon 350, Karl Storz, Tüttlingen, Germany). The surgical procedure was considered to be finished with the removal of the catheters for instrumentation and closure of port sites. The $CO_2$ pneumoperitoneum was maintained until T80 (i.e. during a total time of 60 min).

Adhesions were qualitatively and quantitatively scored blindly one week later during laparotomy using a stereomicroscope (Wild Heerbrugg M7A, Gais, Switzerland). The quantitative scoring system assessed the percentage of the lesions covered by adhesions as follows: adhesion (%)= (sum of the length of the individual attachments/length of the lesion)×100. The qualitative scoring system assessed: extent as measured by a ruler (0: no adhesions; 1: 1-25%; 2: 26-50%; 3: 51-75%; 4: 76-100% of the injured surface involved, respectively), type (0: no adhesions; 1: filmy; 2: dense; 3: capillaries present), tenacity (0: no adhesions; 1: easily fall apart; 2: require traction; 3: require sharp dissection). Total adhesion score was the sum of extent, type, and tenacity. All results represent the average of the adhesions formed at the four individual sites i.e., right and left visceral and parietal peritoneum. The first experiment in this set illustrates the effect of substituting $CO_2$ used for the pneumoperitoneum with $N_2O$ was tested. All mice had a standard bipolar lesion followed by 60 min of pneumoperitoneum either with pure $CO_2$ (n=5, $CO_2$ enhanced adhesion formation) or with pure $N_2O$ (n=5). Adhesion formation assessed qualitatively as a total adhesion score or quantitatively as a proportion decreased from 30±4 to 10±3 and from 70±10 to 15±8% (both P<0.001)

The second experiment resulted in a dose response curve evaluating in comparison of pure $CO_2$ pneumoperitoneum the adhesion reducing effect of adding 5%, 10%, 25%; 50% of $N_2O$ to the $CO_2$ pneumoperitoneum and of using pure $N_2O$. Using pure CO2, CO2 with 5% $N_2O$, with 10% $N_2O$, with 25% $N_2O$, with 50% $N_2O$, or pure N2O respectively, the total adhesion score resulted in 31±4, 12±3, 11±2, 10±5, 11±4 and 10±3 respectively. The quantitative scores were 74±9%, 18±8%, 17±10%, 15±6%, 14±5% and 15±8% respectively.

The third experiment was designed to evaluate whether adding 3% of oxygen to the CO2 pneumoperitoneum and adding N2O had additive effects. Therefore adhesion scores were evaluated after 60 min of pneumoperitoneum with pure CO2, with CO2+3% of oxygen, With CO2+5% N2O, or CO2+3% of oxygen+5% of N2O. (n=5 in each group) The total adhesion scores for CO2, CO2+3% of oxygen, CO2+ 5% N2O and CO2+3% of oxygen+5% of N2O were 32±4, 15±3, 11±2, and 7±2 respectively. The quantitative scores were 77±9%, 35±7%, 17±10% and 10±6% respectively.

In one experiment, the acute inflammatory reaction at the level of the lesions and in the entire peritoneal cavity was investigated. It was found that acute inflammation was decreased importantly by adding 5% NO2 or 3% of Oxygen to the peritoneal cavity.

In another pilot experiment the reduction in tumor implantation rate was demonstrated by adding 5% N2O to the pneumoperitoneum, similar as observed for adding 4% of oxygen.

In one experiment for a control group with a lesion only a comparison was made between the effect of for 60 min leaving the abdomen open at the air, the instillation of a gas flow of 1 l/min deep in the pelvis either with humidified CO2 or with humidified CO2 with 5% of N2O. It should be realized that considering that CO2 and N2O are heavier than air both CO2 or N2O gas pushes the air upwards thus shielding the peritoneal cavity from the air. (densities of CO2, N2O, N2 and O2 are 1.977, 1.98, 1.69 and 1.42 g/l respectively) These experiments confirmed the laparoscopy experiments demonstrating an important increase in adhesions after 60 min exposure to the air, a decrease of these adhesions with the instillation of humidified CO2 and a further reduction in adhesion after the administration of humidified CO2 with 5% of N2O.

In a further set of trials, human patients were treated operatively by laparoscopy using a pneumoperitoneum with 86% $CO_2$, 10% of $N_2O$ and 4% of $O_2$ in combination with full humidification and with a temperature maintained at 31° C. to 32° C. when entering the patient (conditioned group). Furthermore the peritoneal cavity was cooled to 30-32° C. using sprinkling of 2 ml/min of saline at room temperature and rinsing was performed using slightly heparinised saline. A comparison was made with a standard treatment, whereby a pneumoperitoneum with 100% $CO_2$ was used (non-conditioned group). Flow rates were between 3 and 10 liter/min. In a first trial, patients were undergoing deep endometriosis surgery. The trial group received in addition 5 mg of dexamethasone and a hyalobarrier gel at the end of the procedure. In a second trial, patients were undergoing hysterectomy, promontofixation or severe adhaesiolysis (stratification by type) of surgery. A number of parameters were monitored such as postoperative pain, time to first flatus and time to first stools, and the $CO_2$ resorbtion during pneumoperitoneum. In the first trial, endpoints adhesion formation was checked by repeat laparoscopy. In both trials $CO_2$ resorbtion during surgery, postoperative pain assessed by VAS scales and pain killer intake and time to first flatus and time to first stools were monitored.

In the first trial, most of the patients were almost free of adhesions, whereas in the control group severe adhesions were found.

Figure 5:
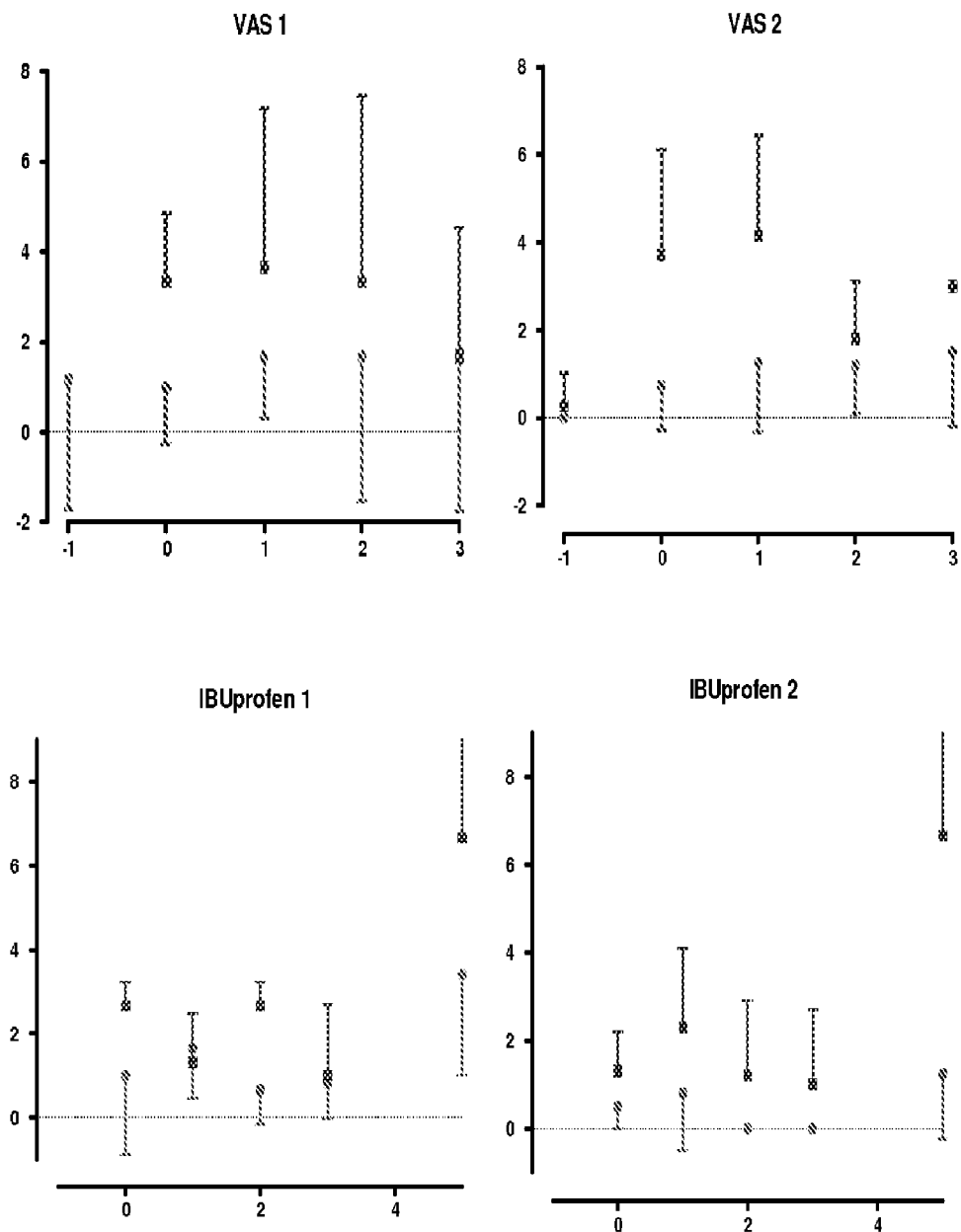
FIG. 5 and FIG. 6 illustrate experimental results for clinical trials on the use of pneumoperitoneum under conditioning according to an embodiments of the present invention.

In both trials post operative pain was evaluated at 3 hours, 12 hours and daily for 4 days after surgery using a VAS scale (Visual Analog Pain Scale) and using the amount of pain killer intake. It was found that post operative pain substantially reduced using a pneumoperitoneum comprising 10% of $N_2O$ in combination with full humidification and temperature control, compared to the use of a $CO_2$ pneumoperitoneum. It was found that the addition of 5% $N_2O$, with or without addition of oxygen, to the pneumoperitoneum resulted in such pain reduction during surgery that it renders laparoscopy under local anaesthesia possible. In FIG. 5, the evaluation of pain on the VAS scale (illustrated by graphs at the top) and the pain killer intake (illustrated by graphs at the bottom) is shown for both trials (trial 1 being illustrated on the left hand side graphs, trial 2 being illustrated on the right hand side). The experimental results indicated by squares illustrate the results for the non-conditioned group whereas the experimental results indicated by the discs illustrate the results for the conditioned group. It can be seen that the pain killer intake is substantially lower for the conditioned group and that the evaluation of pain is more advantageous for the conditioned group.

Figure 6:
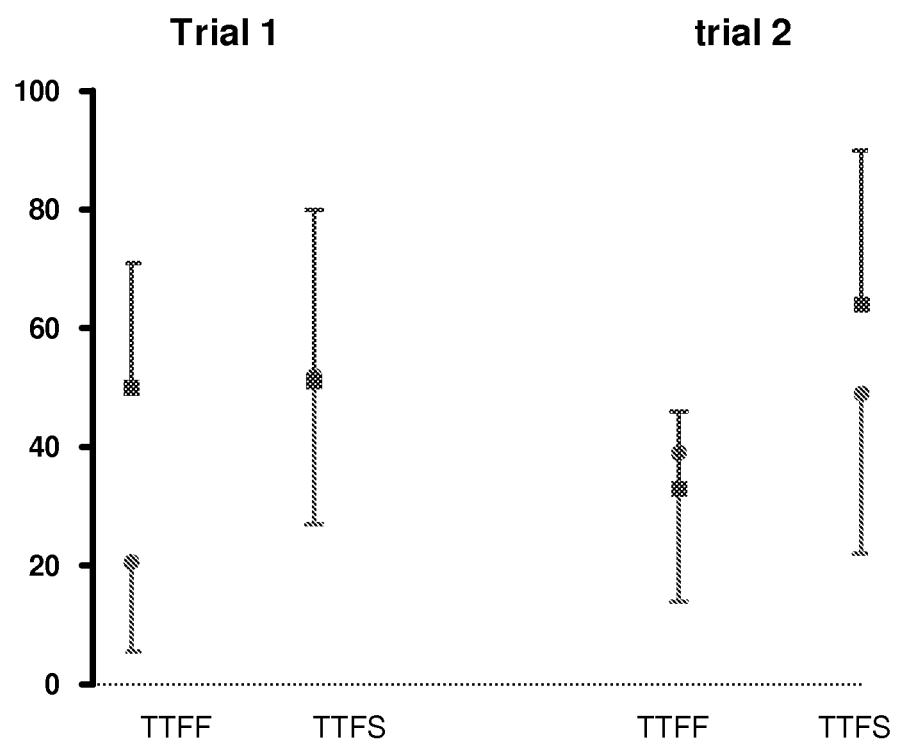

Furthermore, it was found that the time to first flatus and time to first stools significantly reduced. In FIG. 6, for both the first trial (left hand side) and the second trial (right hand side), the time to first flatus (TTFF) and the time to first stools (TTFS) are indicated. The experimental results indicated by squares illustrate the results for the non-conditioned group whereas the experimental results indicated by the discs illustrate the results for the conditioned group. It can be seen that the time to first flatus and time to first stools are clearly shorter in the conditioned group.

It was also found that the progressive increase in $CO_2$ resorbtion during pneumoperitoneum typically occurring during laparoscopy significantly decreases or even almost disappears. Similar effects are expected when using the gas mixture in open surgery.

In conclusion, in both trials the clinical results confirm the beneficial effects of full conditioning in decreasing pain and pain killer intake, in less morbidity, while confirming clinically the beneficial effect upon adhesion formation. In addition it was found that shoulder pain after surgery was no longer observed following conditioning.

These trials furthermore were evidenced by several clinical observations: A patient clearly and correctly indicated which laparoscopy was done under conditioning and which was not, patients having an hysterectomy with conditioning were walking around and planning to leave hospital earlier than patients having a hysterectomy without conditioning, medical staff could indicate correctly which patients received conditioning, anaesthesists confirmed not seeing $CO_2$ resorbtion when conditioning, an observation never made before.

In a further experiment it was found that postoperatively acute inflammation of the body cavity, in the example being the peritoneal lining, was substantially decreased using a gas mixture as pneumoperitoneum comprising a 5% $N_2O$ gas mixture. These effects were seen at the mesothelial level and up to about 1 mm of the submeothelial layers in an experiment using mice.

It is to be noticed that the effect of $N_2O$ has been found surprisingly. Whereas the action of using lower temperatures and addition of oxygen could be explained and taking into account the deleterious effect of mesothelial hypoxia (pure CO2 pneumoperitoneum), mesothelial hyperoxia (more than 10% of oxygen, ROS), dessication and mechanical trauma, the additional effect of adding $N_2O$ seems an effect of protection of mesothelial cells. The mesothelial cell is very fragile and detaches easily. It is believed that $N_2O$ reduces fragility at the level of cell attachment and cell skeleton and can have a stabilizing effect upon the membrane facilitating gliding or affect fibrinolysis.

Thus, whereas the mechanism of action of added $N_2O$ in adhesion prevention is at present not clear, some embodiments of the present invention advantageously result at least in adhesion prevention with in addition safety advantages comparable to $CO_2$ considering the solubilities of $N_2O$, $CO_2$, $N_2$, and $O_2$ being 1.5, 1.45, 0.0391 and 0.0232 respectively). Other optional but correlated advantages are indicated in the embodiments of the present invention.

That the mechanism of action of $N_2O$ is different from the mechanism of action of oxygen is obvious since even a slightly better effect is observed with higher concentrations of $N_2O$ whereas more than 10% of oxygen clearly is deleterious. Given that $CO_2$ is traditionally used to create the pneumoperitoneum for safety reasons (solubility), the lower limit of efficacy of $N_2O$ was investigated to demonstrate specificity of the effect of $N_2O$ upon adhesion formation. During laparoscopy, and during open surgery, however, much higher concentrations of $N_2O$ can safely be used considering that solubility in water of $N_2O$ is comparable to $CO_2$ and much higher than the solubility of $N_2$ and $O_2$. The optimal concentration of $N_2O$ and of $CO_2$ should be determined in future experiment in the human. The upper limit for the $N_2O$ concentration should be limited to maximally 29% and if used together with 4% of oxygen to 25% for safety reasons, since higher concentrations potentially can maintain combustion of gasses from the intestine with some explosion risk.

Furthermore, in some embodiments, control by the anesthetist of the anesthesia may be performed, whereby the use of $N_2O$ in a pneumoperioneum or gas flowing over the body for adhesion prevention is taken into account for controlling the anesthesia, because the resorbtion of $N_2O$ could influence the depth of anesthesia. Resorbtion of $N_2O$ easily can be compensated by reducing the amount of other anesthetic gasses used.

During surgery, the smoke plume generated by vaporization of tissue as occurs during electrosurgery or during $CO_2$ or other laser surgery, is considered potentially harmful even carcinogenic upon inhalation. This together with $N_2O$ being a gas with anesthetic properties, makes it undesirable of let the gas from the operating field flow freely in the air. During laparoscopy aspiration of gas and disposal can easily be done. The gas could be reused in closed circuit after filtrating of particulates but this is not done until today since the gas would have to be recompressed for in an insufflator for endoscopic surgery. In open surgery however, we can take advantage of the density of $CO_2$ and $N_2O$ by constructing an aspiration system, for applying aspiration e.g. a circular aspiration system on and around the operation wound. This not only would prevent the $N_2O$ flowing into the operating theatre but would in addition protect the surgeon from inhalation of particulates generated by vaporization, another advantage.

It should be noted that given the similarity of effects upon the mesothelial tissue between laparoscopic surgery and laparotomy, all beneficial aspects as observed during laparoscopic surgery, such as a reduced temperature, are applicable to open surgery. Considering that probably mesothelial cell trauma plays a role it is not surprising that with $N_2O$ other beneficial effects of adding low concentrations of oxygen, such as reducing tumor implantation can be substituted.

In one embodiment, a method is described wherein provision of nitrous oxide in the pneumoperitoneum or in a gas flow over the open cavity during open surgery is complemented with one or more, advantageously all of the provision of a flow or oxygen gass, cooling, humidification, the provision of ROS scavengers, the provision of calcium channel blockers and of phospholipids, the provision of dexamethasone, the provision of barrier gels and the provision of anti-angiogenic factors and fibroblast manipulation. One or more of the following products may be administered as medicament, i.e. potassium channels; modulators of macrophage activation and leucocyte attraction through cytokines, or their inhibitors, antibodies or inhibitors blocking the effect of VEGF expression; prostaglandin E1; free radical scavengers, lipid peroxysomes; pregnatrienes; calcium antagonists; hypoxia; acidosis; MP; dopamine; and ATP-$MgCl_2$, wherein the method prevents adhesion formation by preventing anoxemia The present invention also relates to a method for applying anesthesia to a living creature. Such a method comprises providing an anesthetic gas or gas mixture for blocking sensation of a living creature. According to embodiments of the present invention, the use of $N_2O$ in a pneumoperitoneum or gas flowing over the body for adhesion prevention thereby is taken into account. More particularly, the method may comprise adjusting a doses of anesthetic gas or gas mixture, e.g. applied in a conventional manner for anesthesia, for blocking sensation of a living creature thereby taking into account the provision of $N_2O$ as a pneumoperitoneum or as gas flowing over the body for adhesion prevention. Adjusting the doses thereby may comprise taking into account resorbtion of $N_2O$ applied as pneumoperitoneum or as gas flow over the open body during open surgery.

The present invention also relates to a conditioning system, whereby the conditioning system is adapted for adding, to the gas used for flowing in or over the cavity where surgery is taking place, between 1% and 29% of $N_2O$. The conditioning system may comprise a controller adapted for controlling the pneumoperitoneum gas as indicated according to any of the embodiments or experiments as described above. The conditioning system thus may assist in performing surgery while preventing mesothelial cell damage. In one embodiment, the conditioning system comprises an endoscopic system or is adapted for co-operating therewith, so as to allow for laparoscopic surgery. In another embodiment, the system is adapted for assisting in open surgery.

The conditioning system also may comprise a number of additional features allowing controlling of the different conditions under which surgery is being performed. One additional component may be a temperature controller and heating and/or cooling element. The conditioner may be adapted for keeping the cavity where surgery is taking place in a temperature range between 25° and 35°, advantageously in a temperature range of 30° to 32°. Under such conditions, cells are more resistant to metabolic damage at lower temperature. Cooling may be performed using a sprinkler, although embodiments of the present invention are not limited thereto.

Advantageously, the cooling is performed separately from the gas conditioning, as using the gas as cooling means, by bringing it to a lower temperature, would result in desiccation due to heating of the gas upon entrance of the cavity. The cooling means thus may be separate from the gas supplying means. For controlling temperature, a temperature sensor also may be present. Such a temperatures sensor may be present at the entrance of the patient but can also be done using a feed forward loop further away from the patient, e.g. based on a known temperature gradient between the temperature measured at the sensor and the temperature at the entrance of the patient.

The conditioning system also may comprise a system for adding oxygen or controlling an oxygen pressure to/in the fluid flowing in or over the cavity where surgery is taking place. For this, between 1% and 10% oxygen may be added, between 2% and 6% oxygen, e.g. 4% oxygen may be added. The latter allows mimicking the natural environment of the cavity where surgery is taking place.

A conditioning system as described above typically can be placed between the insufflator or supply for the gas used for flowing in or over the cavity where surgery is taking place and the patient. The conditioning system in one embodiment may be adapted for first adding $N_2O$ and $O_2$ to the carrier gas, e.g. $CO_2$, which is subsequently humidified and delivered to the patient at 30-32° C. with 100% RH. A separate supply for liquid for cooling may be provided, allowing simultaneously cooling of the cavity, e.g. with 2 ml/min of saline/Hartman at room temperature. Thus the temperature of the incoming gas will also further decrease resulting in slight condensation thus avoiding any desiccation.

The conditioning system and the resulting conditioning has several advantages for the surgery provided, some dependent on the application. Cooling to 30° without desiccation does not affect core body temperature. Conditioning according to embodiments has the advantage that a clear image is maintained. It thereby is an advantage that the image does not deteriorate even after 4 hours of surgery.

The sprinkling can also be used to deliver continuously medicines or other chemical or biological components, such as for example small doses of heparin for preventing clotting and fibrin deposition. In some advantageous embodiments, the conditioning system therefore furthermore comprises a means for adding one or more medicines or drugs or chemicals, e.g. in a controlled amount, to the liquid spread by the sprinkler. By way of illustration, embodiments of the present invention not being limited thereto, a number of medicines or drugs or chemicals that can be added are listed herewith. Anesthetic agents can be added including but not limited to, alcohol, Bupivacaine, Chloroprocaine, Levobupivacaine, Lidocaine, Mepivacaine, Procaine, Ropivacaine and Tetracaine. Analgesic agents can be added which may include but are not limited to, respiratory agents such as Excedrin, Tylenol, DayQuil, NyQuil; centrally acting analgesics such as, Duraclon, Ultrocet and Ultram; miscellaneous analgesics agents such as, Carbatrol, Hyalgan, Lidoderm, Nuropin, Neurontin, Phenegran, and Tegretol; as well as narcotics such as, Nubain, Darvocet, Dilaudid, Lortab, OxyContin, Percocet, and Vicodin. Chemotherapy agents can be added, also known as antineoplastic agents, which may include, but not be limited to, Altretamine, Asparaginase, BCG, Bleomycin sulfate, Busulfan, Carboplatin, Carmustine, Chlorambucil, Cisplatin, Cladribine, Cyclophosphamide, Cytarabine, Decarbazine imidazole carboxamide, Dactinomycin, Daunorubicin-daunomycin, Dexamethasone, Doxombicin, Etoposide-epipodophyllotoxin, Floxuridine, Fluorouracil, Fluoxymesterone, Flutamide, Fludarabine, Goserelin, Hydroxyurea, Idarubicin HCL, Ifosfamide-Isophosphamide, Interferon alfa, Interferon alfa 2a, Interferon alfa n3, Irinotecan, Leucovorin calcium, Leuprolide, Levamisole, Lomustine, Megestrol, Melphalan-L-phenylalanine mustard, L-sarcolysin, Melphalan hydrochloride, MESNA, Mechlorethamine, nitrogen mustard, Methylprednisolone, Methotrexate-Amethopterin, Mitomycin-Mitomycin C, Mitoxantrone, Mercaptopurine, Paclitaxel, Plicamycin-Mithramycin, Prednisone, Procarbazine, Streptozocin, Streptozotocin, Tamoxifen, 6-thioguanine, Thiotepa-triethylene thiophosphoramide, Vinblastine, Vincristine and Vinorelbine tartrate. Anti-infective agents may be added which include those agents classed as antihelminics and antibiotics. Antibiotics may be further classified as aminoglysosides, anti-fungal antibiotics, cephalosporins, b-lactam antibiotics, chloramphenical, macrolides, penicillins, tetracyclines, miscellaneous antibiotics, antituberculosis agents, anti-virals, anti-retrovirals, antimalarials, ouinolones, sulfonamides, sulfones, urinary anti-infectives and miscellaneous anti-infectives. Antihelminics may be added which include by way of example, but are not limited to, Thiabendazole. Aminoglycosides may be added which include by way of example, but are not limited to, Amikacin, Gentamicin, Neomycin, Streptomycin and Tobramycin. Antifungal antibiotics may be added which may include but are not limited to, Amphotericin B, Amphotericin B5 Lipid formulation T.E., Fluconazole, Flucytosine, Griseofulvin, Itraconazole, Ketoconazole, Nystatin, and Terbinafine. Cephalosporins may be added which may include but are not limited to Cefaclor, Cefazolin, Cefepime, Cefixime, Cefonicid, Cefotaxine, Cefpodoxine, Cefprozil, Ceftazidine, Ceftriaxone, Cefuroxime, Cephalexin, and Cephradine. B-Lactam antibiotics may be added which may include but are not limited to Aztreonam, Cefotetan, Cefoxitin, and Imipenem/Cilastatin. Chloroamphenicol may be adde which may include but are not limited to, Chloramphenicol, Chloramphenicol Palmitate, and Chloramphenicol Succinate. Macrolides may be added which may include but are not limited to Azithromycin, Clarithromycin, Erythromycin, Erythromycin Ethyl Succinate and Erythromycin Lactobionate. Tetracyclines may be added which may include but are not limited to Demeclocycline, Doxycycline, Minocycline and Tetracycline. Miscellaneous antibiotics may be used which may include but are not limited to, Bacitracin, Clindamycin, Polymyxin B, Spectinomycin and Vancomycin. Antituberculosis agents may be used which may include but are not limited to Ethambutol, Isoniazid, Pyrazinamide, Rifabutin and Rifampin. Antivirals may be used which may include but are not limited to Acyclovir, Amantadine, Famciclovir, Foscarnet, Ganciclovir, Ribavirin, Valacyclovir and Valganciclovir. Antiretrovirals may be used which may include but are not limited to Abacavir, Amprenavir, Didanosine, Efavirenz, Indinavir, Lamivudine, Loopinavir, Nelf[iota]navir, Nevirapine, Ritonavir, Saquinavir, Stavudine, Zalcitabine and Zidovudine. Antimalarials may be added which may include but are not limited to Chloroquine, Hydroxychloroquine, Pyrimethamine and Quinine. Quinolones may be used which may include but are not limited to Gatifioxacin, Levofloxacin and Ofloxacin.

Sulfonamides may be added which may include but are not limited to Sulfadiazine, Sulfamethoxazole, Sulfasalazine and Sulfisoxazole. Sulfones may be added which may include but are not limited to Dapsone. Urinary anti-infectives may be used which may include but are not limited to Nitrofurantoin.

Miscellaneous anti-infectives may be used which may include but are not limited to Clofazamine, Co-trimoxazole, Metronidazole and Pentamidine.

Anti-adhesions agents may be used which may include but are not limited to Aspirin, Calcium channel blockers, Carboxymethylcellulose, Chondroitin sulfate, Corticosteroids, Chymase inhibitors, Dextran, Dialysis solution, Diphenhydramine, Fibrin glue, Haparin, Hyaluronic acid, L-Arginine, Methylene blue, Mifepristone, Mitomycin C, NSAIDs, Octreotide, Pentoxifylline, Peritoneal transplant, Photopolymerized hydrogel, Polyethylene glycol, P[omicron]lyoxamer, Ringers lactate, Saline, Surfactant and tissue plasminogen activator. Also known are solutions or gels such as Hyaluronic acid, Hyalutronate-carboxymethylcellulose, Carboxymethylcellulose, Polyethylene glycol, Dextran 70 and Icodextrin 4%. Also known are commercial anti-adhesion barriers such as hyaluronate-carboxymethylcellulose, oxidized regenerated cellulose, polyethylene oxide-oxidized regenerated cellulose, expanded polytetrafluoroethylene and pericardial patch. The use of the above medicines, drugs or chemicals may require shredding, pulverizing or powdering together with mixing them with a liquid to make them usable in the present invention.

It also is advantageous that the components of the conditioning do not substantially interfere with the tools to be used by the surgery, so that no disturbing effect is induced for the surgeon.

It is an advantage of embodiments according to the present invention that mesotheleal cells can be better protected.

It is an advantage of embodiments according to the present invention that pain can be substantially reduced, resulting in the possibility for performing laparoscopy under local anesthesia.

It is an advantage of embodiments according to the present invention that $CO_2$ resorbtion can be reduced or avoided, permitting longer surgery in more steep Trendelenburg.

It is an advantage that using embodiments of the present invention pain can be reduced during the first three days after surgery and that pain killer intake can be reduced.

It is an advantage of embodiments according to the present invention that the time to first flatus and time to first stools after surgery can be decreased.

It is an advantage of embodiments according to the present invention that adhesion formation can substantially reduced, e.g. over 80%, and in combination with other features such as barriers, even over 90% compared to conventional laparoscopy without such features.

It is an advantage of embodiments according to the present invention that tumor cell implantation can be reduced, e.g. by at least 75%, e.g. at least 90%, as evidenced in animal models.

It is an advantage of embodiments according to the present invention that little acute inflammation is present, e.g. substantially less than obtained using conditioning without the use of $N_2O$.

In one aspect, the present invention also relates to a conditioning system for conditioning a cavity wherein surgery is or will be performed, e.g. during pneumoperitoneum or in open surgery. The conditioning system according to embodiments of the present invention comprises a sprinkler for moistening the cavity, e.g. for cooling the cavity to a predetermined temperature. In one embodiment, the conditioning system comprises an endoscopic system or is adapted for co-operating therewith, so as to allow for laparoscopic surgery. In another embodiment, the system is adapted for assisting in open surgery. The system furthermore optionally comprises other components such as for example a controller for controlling a gas mixtures for flowing over a cavity wherein surgery is or will be performed such that it comprises between 1% and 29% of $N_2O$, a controller for controlling a gas mixture for flowing over a cavity wherein surgery is or will be performed such that it comprises between 1% and 10% oxygen, a controller for controlling temperature or one or more of such features or other features as described in a conditioning means according to the present invention.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A method for reducing or preventing mesothelial cell damage during surgery comprising the steps of:
   mixing a carrier gas and nitrous oxide gas in a mixer to form a medicament, wherein the nitrous oxide gas is between 5 and 20 volume percent, and
   applying the medicament during surgery by flowing the medicament in or over a cavity over the mesothelial cells during surgery in a cavity to reduce or prevent mesothelial cell damage.

2. A method for reducing or preventing mesothelial cell damage during surgery comprising the steps of:
   mixing a carrier gas and nitrous oxide gas in a mixer to form a medicament, wherein the nitrous oxide gas is between 5 and 10 volume percent, and
   applying the medicament during surgery by flowing the medicament in or over a cavity over the mesothelial cells during surgery in a cavity to reduce or prevent mesothelial cell damage.

3. The method of claim 1, wherein the carrier gas is carbon dioxide gas.

4. The method of claim 1, wherein the solubility of the carrier gas is larger than 0.5 g/l in water.

5. The method of claim 1, wherein applying the medicament comprises flowing the medicament during pneumoperitoneum.

6. The method of claim 1, wherein applying the medicament comprises flowing the medicament during open surgery.

7. The method according to claim 1, wherein applying the medicament during surgery furthermore comprises applying the medicament for reducing or preventing pain.

8. The method according to claim 1, wherein applying the medicament during surgery furthermore comprises applying the medicament for reducing or preventing acute inflammation.

9. The method according to claim 1, wherein applying the medicament during surgery furthermore comprises applying the medicament for reducing or preventing CO2 resorbtion.

10. The method according to claim 1, wherein applying the medicament during surgery furthermore comprises applying the medicament for reducing tumor implantation reduction.

11. The method according to claim 1, wherein applying the medicament during surgery furthermore comprises applying the medicament for reducing or preventing adhesion formation.

12. The method according to claim 1, further comprising the step of removing environmental air or unwanted gasses present in the cavity.

13. The method according to claim 1, wherein applying the medicament during surgery includes deliberately insufflating the cavity during the surgery.

14. The method according to claim 6, wherein during open surgery, when the cavity is opened and exposed to environmental air, the medicament flows over the cavity removing the environmental air.

15. The method according to claim 2, wherein the medicament further comprises a concentration of oxygen in the range of 1 to 10%.

16. The method according to claim 15, wherein the concentration of oxygen is in the range of 3-4%.

17. The method according to claim 16, further comprising the step of maintaining a temperature of the medicament between 31-32° C. and cooling the cavity to 30-32° C.

18. The method according to claim 2, wherein the surgery is a laparoscopy.

19. The method according to claim 6, wherein the open surgery comprises providing an incision through a wall of the cavity.

* * * * *